United States Patent
Park et al.

(10) Patent No.: US 8,685,338 B2
(45) Date of Patent: Apr. 1, 2014

(54) OPEN-AND-CLOSE CONTROLLABLE ODOR COMPOUND RELEASE DEVICE AND METHOD OF MANUFACTURE

(75) Inventors: Jong-jin Park, Hwaseong-si (KR); Sung-ho Jin, San Diego, CA (US); Kyu-hyun Im, Yongin-si (KR); Jong-min Kim, Yongin-si (KR)

(73) Assignees: Samsung Electronics Co., Ltd., Suwon-si (KR); The Rgegents of The University of California, Oakland, CA (US)

( * ) Notice: Subject to any disclaimer, the term of this patent is extended or adjusted under 35 U.S.C. 154(b) by 89 days.

(21) Appl. No.: 13/074,140

(22) Filed: Mar. 29, 2011

(65) Prior Publication Data
US 2012/0076695 A1     Mar. 29, 2012

(30) Foreign Application Priority Data
Sep. 27, 2010   (KR) .................. 10-2010-0093295

(51) Int. Cl.
- *A61L 9/00* (2006.01)
- *B01D 47/06* (2006.01)
- *B05B 5/00* (2006.01)
- *A01M 19/00* (2006.01)

(52) U.S. Cl.
USPC ............ 422/306; 261/76; 261/78.1; 239/690; 43/125; 43/129; 428/402.2

(58) Field of Classification Search
USPC .............. 422/1, 5, 28, 125, 305, 306; 261/76, 261/78.1, DIG. 17; 239/690, 34; 43/1, 125, 43/129; 428/402.2
See application file for complete search history.

(56) References Cited

U.S. PATENT DOCUMENTS

| | | | |
|---|---|---|---|
| 2004/0107808 A1 | 6/2004 | Calwell | |
| 2004/0210289 A1* | 10/2004 | Wang et al. | 607/116 |
| 2006/0052020 A1* | 3/2006 | Marmarpoulos | 442/301 |
| 2008/0313789 A1* | 12/2008 | Manne | 2/209.13 |

FOREIGN PATENT DOCUMENTS

| | | | | |
|---|---|---|---|---|
| JP | 05-003910 | * | 1/1993 | ........... A61L 9/12 |
| JP | 05-003910 A | | 1/1993 | |
| JP | 07-077463 A | | 3/1995 | |
| JP | 2007-168258 A | | 7/2007 | |
| KR | 20-0248661 Y1 | | 11/2001 | |
| KR | 10-0458857 B1 | | 12/2004 | |
| KR | 10-0499588 B1 | | 7/2005 | |

(Continued)

OTHER PUBLICATIONS

Japan Patent Office English Translation of the "Detailed Description Section" of JP 05-003910.*

(Continued)

*Primary Examiner* — Monzer R Chorbaji
(74) *Attorney, Agent, or Firm* — Sughrue Mion, PLLC

(57) ABSTRACT

An odor compound release device includes a support that is deformed when an external stimulus is applied, and when the external stimulus is not applied, restored to its original state. A plurality of spaces are located in the support, have upper portions closed by the support, and are to be filled with odor compounds, wherein the upper portions are opened or closed by deformation or restoration of the support due to the application of the external stimulus. A member that is located in the support or on a surface of the support and applies the external stimulus to the support.

28 Claims, 11 Drawing Sheets

(56) References Cited

FOREIGN PATENT DOCUMENTS

| KR | 20-0393995 Y1 | 8/2005 |
|---|---|---|
| KR | 1020050086726 A | 8/2005 |
| KR | 1020060011619 A | 2/2006 |
| KR | 20-0424070 Y1 | 8/2006 |
| KR | 10-0623932 B1 | 9/2006 |

OTHER PUBLICATIONS

Todd Hoare, et al.; "A Magnetically Triggered Composite Membrane for On-Demand Drug Delivery"; American Chemical Society; 2009; vol. 9 No. 10; pp. 3651-3657.

Jo, Eunmin, et al., "Core-Sheath Nanofibers Containing Colloidal Arrays in the Core for Programmable Multi-Agent Delivery," Wiley-VCH Verlag GmbH & Co. KGaA, Advanced Materials, vol. 21, 2009, pp. 968-972.

Hu, Shang-Hsiu, et al., "Controlled Rupture of Magnetic Polyelectrolyte Microcapsules for Drug Delivery," American Chemical Society, Langmuir, vol. 24, No. 20, Sep. 23, 2008, pp. 11811-11818.

Slowing, Igor, et al., "Mesoporous Silica Nanoparticles for Drug Delivery and Biosensing Applicatoins," Wiley-VCH Verlag GmbH & Co. KGaA, Advanced Functional Materials, vol. 17, 2007, pp. 1225-1236.

Hillebrenner, Heather, et al., "Corking Nano Test Tubes by Chemical Self-Assembly," American Chemical Society, JACS, vol. 128, No. 13, Mar. 15, 2006, pp. 4236-4237.

Skirtach, Andre G., Et al., "The Role of Metal Nanoparticles in Remote Release of Encapsulated Materials," American Chemical Society, Nano Letters, vol. 5, No. 7, Jun. 25, 2005, pp. 1371-1377.

Soppimath, Kumaresh S., et al., "pH-Triggered Thermally Responsive Polymer Core-Shell Nanoparticles for Drug Delivery," Wiley-VCH Verlag GmbH & Co. KGaA, Advanced Materials, vol. 17, No. 3, Feb. 10, 2005.

Tao, Sarah L., et al., "Microfabrication of Multilayer, Asymmetric, Polymeric Devices for Drug Delivery," Wiley-VCH Verlag GmbH & Co. KGaA, Advanced Materials, vol. 17, 2005, pp. 1625-1630.

Barbe, Christophe, et al., "Silica Particles: A Novel Drug-Delivery System," Wiley-VCH Verlag GmbH & Co. KGaA, Advanced Materials, vol. 16, No. 21, Nov. 4, 2004, pp. 1959-1966.

Lee, Kuen Yong, et al., "Controlled Drug Delivery from Polymers by Mechanical Signals," Wiley-VCH Verlag GmbH, Advanced Materials, vol. 13, No. 11, Jun. 5, 2001, pp. 837-839.

Jo, Eunmin, et al., "Core-Sheath Nanofibers Containing Colloidal Arrays in the Core for Programmable Multi-Agent Delivery," Wiley-VCH Verlag GmbH & Co. KGaA, Advanced Materials, vol. 21, Dec. 18, 2008, pp. 968-972.

Slowing, Igor I., et al., "Mesoporous Silica Nanoparticles for Drug Delivery and Biosensing Applicatoins," Wiley-VCH Verlag GmbH & Co. KGaA, Advanced Functional Materials, vol. 17, Apr. 20, 2007, pp. 1225-1236.

Tao, Sarah L., et al., "Microfabrication of Multilayer, Asymmetric, Polymeric Devices for Drug Delivery," Wiley-VCH Verlag GmbH & Co. KGaA, Advanced Materials, vol. 17, Mar. 29, 2005, pp. 1625-1630.

\* cited by examiner

OPEN-AND-CLOSE CONTROLLABLE ODOR COMPOUND RELEASE DEVICE AND METHOD OF MANUFACTURE

CROSS-REFERENCE TO RELATED APPLICATIONS

This application claims the benefit of Korean Patent Application No. 10-2010-0093295, filed on Sep. 27, 2010, in the Korean Intellectual Property Office, the disclosure of which is incorporated herein in its entirety by reference.

BACKGROUND

1. Field

The present disclosure relates to devices for emitting an odor compound such as fragrance, and more particularly, to an open-and-close controllable odor compound release device, and method of manufacturing an odor compound release device.

2. Description of the Related Art

The combination of fragrance release and electronic devices may occur, for example, in fragrance effects for four-dimensional movies, fragrance reproduction in display devices, fragrance transfer through mobile phones, and the like.

However, in related art fragrance release devices, once capsules or containers have been opened, the odor compound contained therein is completely emitted. Thus, it is difficult to repeatedly emit fragrance while controlling the release time and release amount of the fragrance.

SUMMARY

Provided are open-and-close controllable odor compound release devices configured to emit fragrance while controlling the release time and the release amount, and a method of manufacturing an odor compound release device.

According to an aspect of an embodiment, an odor compound release device includes a support that is deformed when an external stimulus is applied, and when the external stimulus is not applied, restored to its original state; a plurality of spaces that are located in the support, have upper portions closed by the support, and are configured to be filled with odor compounds, wherein the upper portions are can be opened or closed by deformation or restoration of the support due to the application of the external stimulus; and a member that is located in the support or on a surface of the support and applies the external stimulus to the support.

The support may include a natural rubber or a synthesized rubber. The synthesized rubber may be a material selected from the group consisting of a block copolymer, a fluorine rubber, a silicone rubber, and isoprene. The member may be a thermal wire for transferring heat to the support. The thermal wire may be disposed under the spaces.

The support may include a material that is deformable when a voltage is applied thereto. The support may include a conductive polymer, a liquid crystalline elastomer, or a dielectric elastomer. The member may be an electrode for applying voltage to the support. The electrode may be located on each of upper and lower surfaces of the support.

The support may include a temperature sensitive phase transition polymer. The support may include poly(N-isopropylacrylamide) (PNIPAM). The member may be magnetic nanoparticles that are dispersed in the support, and may inductively heat the support when an external magnetic field is applied to the magnetic nanoparticles.

According to an aspect of another embodiment, there is provided an odor compound release device including a substrate having an upper portion having a plurality of spaces that are to be filled with an odor compound; a capping layer formed on a upper surface of the substrate, wherein portions of the capping layer contact each other above the spaces to close inlets of the spaces, but when an external stimulus is applied, the capping layer is deformed to separate the contact portions, and when the external stimulus is not applied, the contact portions are restored to their original states, so that the separated portions contact each other, thereby enabling opening or closing of the inlets of the spaces; and a member that is located in the capping layer or on a surface of the capping layer and applies the external stimulus to the capping layer.

The capping layer may include a natural rubber or a synthesized rubber. The member may be a thermal wire for transferring heat to the capping layer.

The capping layer may include a material that is deformable when a voltage is applied thereto. The capping layer may include a conductive polymer, a liquid crystalline elastomer, or a dielectric elastomer. The member may be an electrode for applying voltage to the capping layer.

The capping layer may include a temperature-sensitive phase transition polymer. The capping layer may include poly(N-isopropylacrylamide) (PNIPAM). The member may include magnetic nanoparticles that are dispersed in the capping layer and inductively heat the capping layer when an external magnetic field is applied to the magnetic nanoparticles.

The spaces are aligned in a matrix. The member may be aligned such that the external stimulus is independently applied to each row or each column of the matrix.

According to an aspect of another embodiment, a method of manufacturing an odor compound release device includes adding a rubber solution to a container and immersing a first portion of a template in the solution in the container, and heat-treating the rubber solution, and removing the template to form a space in a first portion of a support, the space having an inlet that is configured to be opened in response to a stimulus. The method may also include adding the rubber solution to the container to form a second portion of the support, and attaching the first portion of the support to the second portion of the support, forming a member on at least one of the first portion and the second portion, and injecting an odor compound into the space of the support. The member is configured to apply the stimulus to the support, so as to open the inlet and release the odor compound.

BRIEF DESCRIPTION OF THE DRAWINGS

These and/or other aspects will become apparent and more readily appreciated from the following description of the embodiments, taken in conjunction with the accompanying drawings, in which.

DETAILED DESCRIPTION

Figure 1:
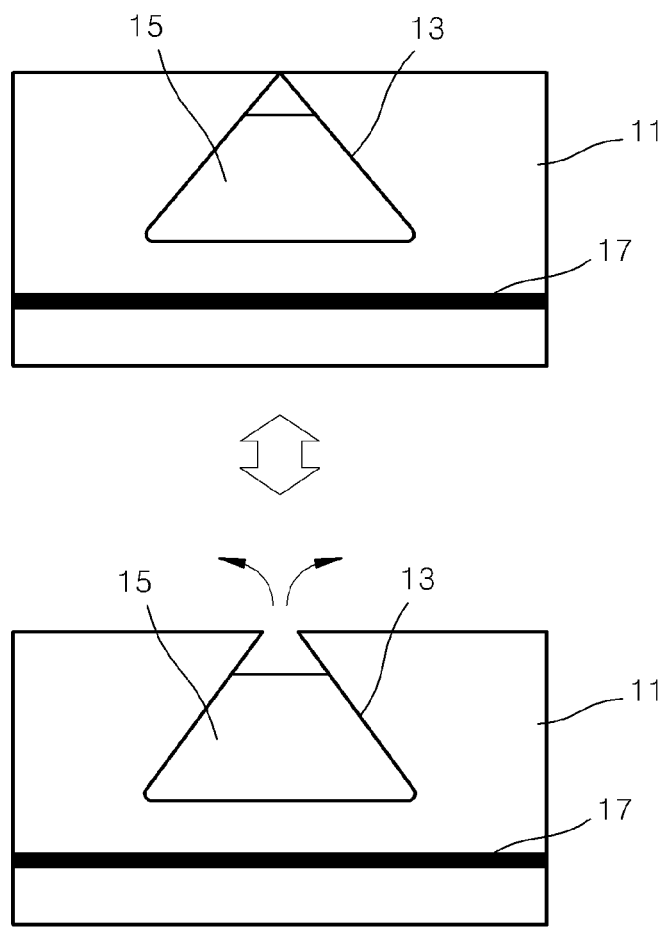
FIG. 1 is a schematic view of an odor compound release device according to an embodiment.

Reference will now be made in detail to embodiments, examples of which are illustrated in the accompanying drawings, wherein like reference numerals refer to like elements throughout. In this regard, the described embodiments may have different forms and should not be construed as being limited to the descriptions set forth herein. Accordingly, the embodiments are merely described below, by referring to the figures, to explain aspects of the present description.

The term "odor compound" used herein refers to a compound that emits fragrance or shows pharmaceutical effects when the compound evaporates.

FIG. 1 is a schematic view of an odor compound release device according to an embodiment. Referring to FIG. 1, a support 11 has an open space 13 therein, and a thermal wire 17 is disposed under the space 13. The space 13 is to be filled with an odor compound, and portions of the support 11 may move to contact each other to form an interface, thereby closing an inlet of the space 13. The space 13 may have a diameter of a few micrometers or a few millimeters. In this regard, the interface at the inlet of the space 13 is not sealed, so that when power is applied thereto, the portions of the support 11 are separated from each other, thereby opening the inlet of the space 13.

The support 11 may be formed of rubber, for example, a natural rubber or a synthesized rubber. The synthesized rubber may be a block copolymer, a fluorine rubber, a silicon rubber, polybutadiene, or polyisoprene. Examples of a block copolymer include styrene-butadiene-styrene (SBS) rubber, styrene-ethylene-butadiene-styrene (SEBS) rubber, ethylene-propylene copolymer, ethylene-butene-diene copolymer, ethylene-propylene-diene copolymer, and hydrogenated styrene-butadiene copolymer. Besides the compounds described above, the synthesized rubber may also be polysiloxane, polymetacrylamide, nitrile rubber, acrylic rubber, polyethylene tetrafluoride, polybutene, polypentene butyl rubber, polymethylpentene, styrene hydrogenated polyisoprene, or hydrogenated polybutadiene. The silicon rubber may be, for example, polydimethylsiloxane (PDMS). However, the composition of the support 11 is not limited thereto.

The thermal wire 17 may be a wire that dissipates heat due to an electrical resistance when a current flows therethrough. The thermal wire 17 may be, for example, a nichrome wire.

Rubber molecular behavior may differ according to temperature. Rubber has a glass state at a glass transition temperature (Tg) or lower. However, at a temperature higher than the Tg, rubber has a rubbery state and thus, when there is an interface, an interfacial contact may be improved. Accordingly, at a temperature higher than the glass transition temperature Tg, a sealing capability of rubber is improved, and thus, rubber is used as a cover for a container containing a liquid. That is, a support formed of rubber has a rubbery elastic modulus at room temperature that is higher than the glass transition temperature Tg, that is, a soft state, and thus the inlet of the space 13 has a good sealing state. However, when a current flows through the thermal wire 17 and the support 11 is heated, the soft state is changed to a flow state. In this case, the inlet of the space 13 is further softened and thus, an odor compound 15 filling the space 13 may be released from the space 13. Also, when the current flow in the thermal wire 17 is stopped, the temperature of the support 11 decreases and thus, the rubber state of the support 11 changes from a flow state to a soft state, thereby allowing the support 11 to have the elasticity to close the inlet of the space 13. Accordingly, by turning on or off the current supply for generating heat in the thermal wire 17, the rubber molecular behavior of the support 11 changes from a soft state to a flow state or vice versa, thereby opening or closing the inlet of the space 13. By doing so, the release of the odor compound 15 may be controlled.

Figure 2:
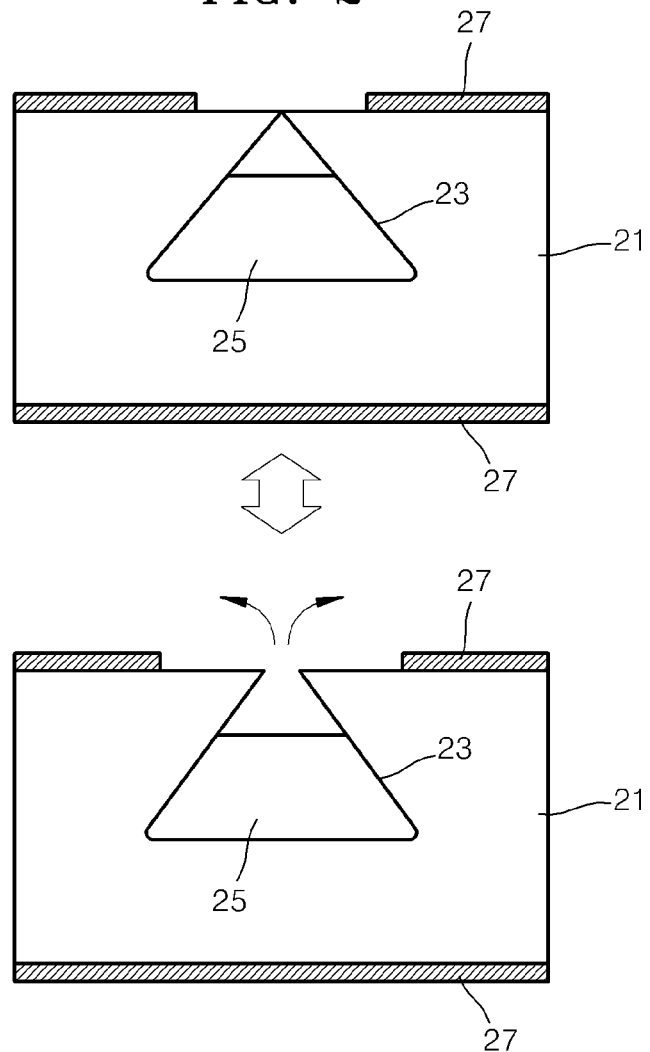
FIGS. 2 and 3 are schematic views of odor compound release devices according to other embodiments.
Figure 3:
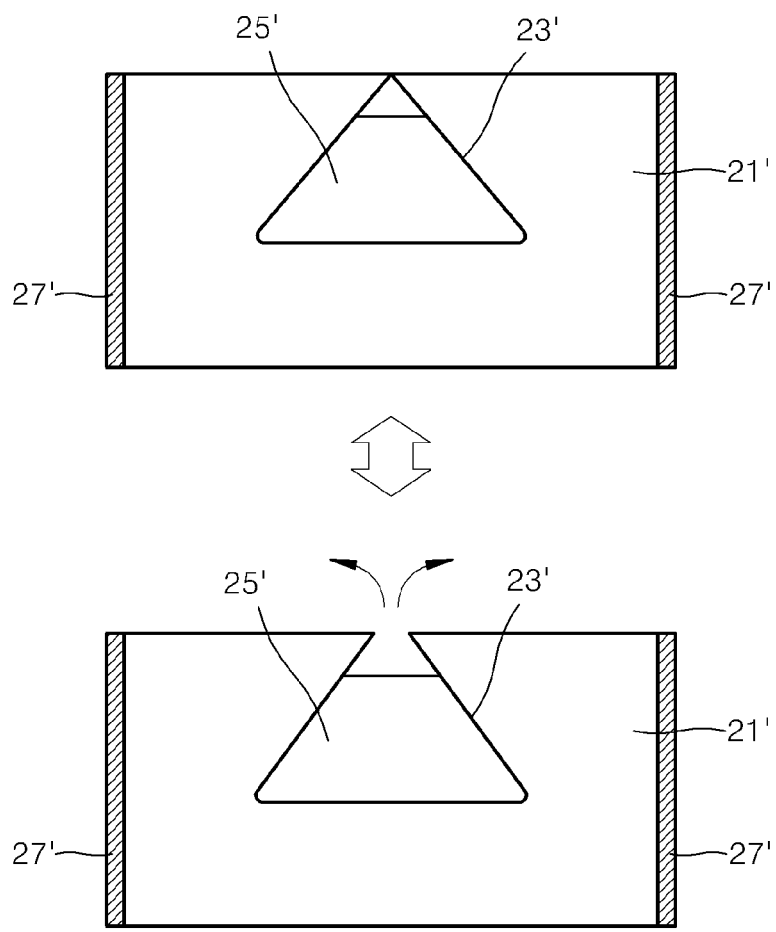

FIGS. 2 and 3 are schematic views of odor compound release devices according to other embodiments. A support 21 has a space 23 therein, and electrodes 27 for applying a voltage are formed respectively on upper and lower surfaces of the support 21. The space 23 is to be filled with an odor compound, and portions of the support 21 contact each other to form an interface, thereby closing an inlet of the space 23. The space 23 may have a diameter of a few micrometers or a few millimeters. In this regard, the interface at the inlet of the space 23 is not sealed, so that when power is applied thereto, the contact portions of the support 23 are separated from each other, thereby opening the inlet of the space 23. Alternatively, as illustrated in the embodiment of FIG. 3, electrodes 27' may be respectively located on side surfaces of a support 21' having a space 23' therein.

Supports 21 and 21' may be formed of a material that has a deformable state when voltage is applied thereto. The material will now be referred to as a voltage deformable material. The supports 21 and 21' may be formed of, for example, a mixture including a conductive polymer and an elastic body, a liquid crystalline elastomer, or a dielectric elastomer.

Regarding a conductive polymer, a volumetric change occurs mainly due to flow of ions during oxidation and reduction, thereby causing contraction and expansion. Regarding a liquid crystalline elastomer, when a voltage is applied to a liquid crystalline elastomer, phase transition or orientation change of liquid crystals occurs, thereby causing deformation. Regarding a dielectric elastomer, charge separation occurs due to an electric field, and an elastic body is compressed due to the formed attractive force, thereby causing deformation.

The conductive polymer may be, for example, a homopolymer or copolymer, such as polyacetylene (PA), polythiophene (PT), poly 3-alkyl thiophene (P3AT), polypyrrole (PPY), polyisothianaphthelene (PITN), polyethylene dioxythiophene (PEDOT), poly(para-phenylene) vinylene (PPV), poly (2,5-dialkoxy para-phenylene vinylene), polyparaphenylene (PPP), polyparaphenylene sulphide (PPS), polyheptadiyne (PHT), or poly 3-hexyl thiophene (P3HT), or polyaniline (PANI). However, the conductive polymer is not limited thereto.

The liquid crystalline elastomer may be, for example, a monopolymer formed by curing polysiloxane, poly dimethyl siloxane, tetramethylenecyclosiloxane, or hydro-oligo dimethylsiloxane by hydrosilylation, or a copolymer of the monomer and polyester.

The dielectric elastomer may be, for example, silicone or acryl rubber.

The electrodes 27 and 27' may be formed of a conductive material, such as metal, for applying a voltage to the supports 21 and 21'. The electrodes 27 and 27' may be disposed in any of various locations that enable inlets of the spaces 23 and 23' to be opened when the supports 21 and 21' are deformed by voltage application.

When voltage is not applied, the supports 21 and 21' are not deformed and thus the inlets of the spaces 23 and 23' are maintained closed. However, when voltage is applied, the supports 21 and 21' are constricted and thus the inlets of the spaces 23 and 23' are opened and odor compounds 25 and 25' filling the spaces 23 and 23' are released to the outside. When the voltage application is stopped, the supports 21 and 21' return to their original states from the constriction state, thereby closing the inlets of the spaces 23 and 23'. Accordingly, by turning on or off voltage application through the electrodes 27 and 27', the inlets of the spaces 23 and 23' are opened or closed. As a result, the release of the odor compounds 25 and 25' is controllable.

Figure 4:
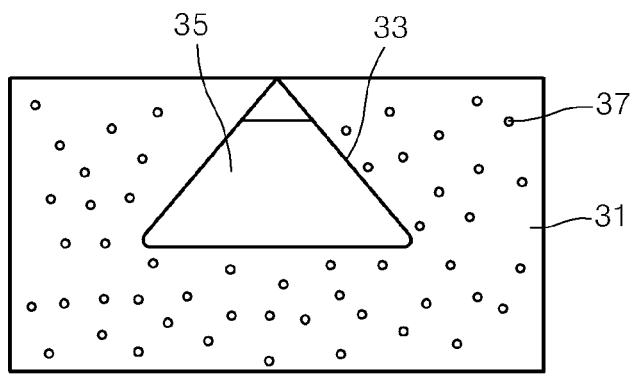
FIG. 4 is a schematic view of an odor compound release device according to another embodiment.
Figure 4:
Figure 4:
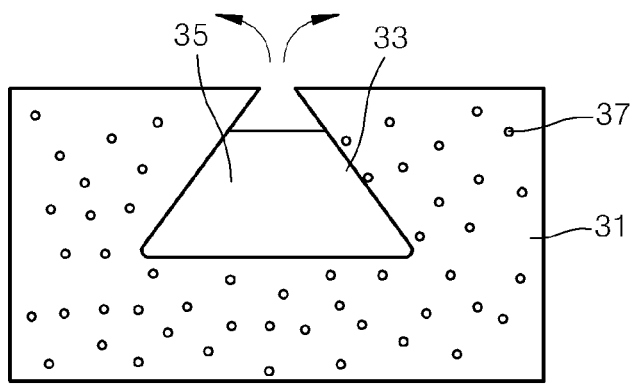

FIG. 4 is a schematic view of an odor compound release device according to another embodiment. A support 31 has a space 33 therein. The space 33 is to be filled with an odor compound, and an upper portion of the space 33 is closed by contacting portions of the support 31. The space 33 may have a diameter of a few micrometers or a few millimeters. In this regard, the contact portions of the support 31 are not sealed to each other, and thus, when a power is applied thereto, the contact portions are separated from each other, thereby opening the inlet of the space 33.

The support 31 may be formed of a temperature-sensitive phase transition polymer including magnetic nanoparticles 37. The temperature-sensitive phase transition polymer has a hydrophilic state at a temperature lower than a phase transition temperature and thus absorbs water to expand, and at a temperature equal to or higher than the phase transition temperature, the temperature-sensitive phase transition polymer has a hydrophobic state, and releases water and contracts. The temperature-sensitive phase transition polymer may absorb water surrounding the support 31. The temperature-sensitive phase transition polymer may be, for example, poly(N-isopropylacrylamide) (PNIPAM). A phase transition temperature of PNIPAM is about 37° C.

At room temperature, the support 31 has a hydrophilic state and expands, thereby closing the inlet of the space 33. If an external magnetic field is applied to the support 31, the magnetic nanoparticles 37 in the support 31 are subjected to inductive heating and thus, the temperature of the support 31 may increase to a temperature equal to or higher than a phase transition temperature. In this case, the support 31 changes to a hydrophobic state and contracts, thereby opening the inlet of the space 33 and releasing an odor compound 35 to the outside. When the supply of the external magnetic field is stopped, the inductive heating of the magnetic nanoparticles 37 is stopped and the temperature of the support 31 is decreased to a temperature lower than the phase transition temperature. At a temperature lower than the phase transition temperature, the support 31 has a hydrophilic state and expands, thereby closing the inlet of the space 33. Accordingly, by turning on or off the supply of an external magnetic field, the inlet of the space 33 is opened or closed. By doing so, the release of the odor compound 35 is controllable. Alternatively, as in the embodiment described above with reference to FIG. 1, instead of the magnetic nanoparticles 37, a thermal wire (not shown) may be introduced into the support 31 formed of the temperature-sensitive phase transition polymer to control the temperature of the support 31, thereby controlling the release of the odor compound 35.

Hereinbefore, one support has one space in the previously described embodiments. However, one support may have a plurality of spaces. In addition, the spaces may be aligned in a matrix.

Figure 5:
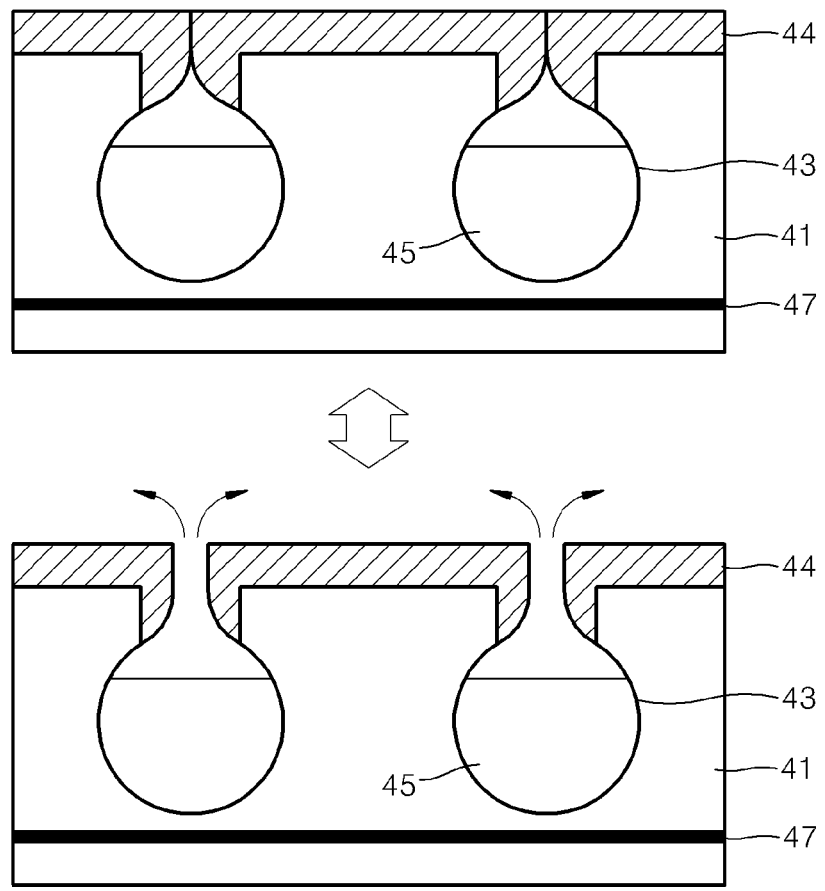
FIG. 5 is a schematic view of an odor compound release device according to another embodiment.

FIG. 5 is a schematic view of an odor compound release device according to another embodiment. A substrate 41 has a plurality of spaces 43 therein, and a thermal wire 47 may be disposed under the spaces 43. The spaces 43 are to be filled with an odor compound. The spaces 43 may have a diameter of a few micrometers or a few millimeters. A capping layer 44 may cover a surface of the substrate 41, and portions of the capping layer 44 contact each other to close inlets of the spaces 43. In this regard, the contact portions of the capping layer 44 are not sealed, so that when power is applied thereto, the portions of the capping layer 44 are separated from each other, thereby opening the inlets of the spaces 43.

The substrate 41 may be formed of materials such as plastic, metal, silicon, etc. The spaces 43 in the substrate 41 may be formed by, for example, a microelectromechanical system (MEMS) process. Alternatively, the substrate 41 may be an anodic aluminum oxide substrate, and the spaces 43 in the anodic aluminum oxide substrate may be formed by anodic oxidation. The spaces 43 may be aligned in a matrix.

The capping layer 44 may be formed of rubber. The capping layer 44 may be, for example, a natural rubber or a synthesized rubber. The synthesized rubber may be a block copolymer, a fluorine rubber, isoprene, or silicone rubber. Examples of a block copolymer include a SBS rubber, a SEBS rubber. The silicone rubber may be, for example, PDMS.

The thermal wire 47 may be a wire that dissipates heat due to an electrical resistance when a current flows therethrough. The thermal wire 47 may be, for example, a nichrome wire.

The capping layer 44 has a rubbery elastic modulus at room temperature and thus, the inlets of the spaces 43 retain excellent sealing states. If a current flows through the thermal wire 47, the thermal wire 47 is heated, thereby heating the substrate 41 and the capping layer 44. When the capping layer 44 is heated, rubber changes from a soft state to a flow state, thereby weakening the sealing state of the inlets of the spaces 43 and thus releasing an odor compound 45 from the spaces 43. When the current supply to the thermal wire 47 is stopped, the substrate 41 and the capping layer 44 are cooled, thereby changing the rubber state of the capping layer 44 from a flow state into a soft state. Thus, the capping layer 44 regains elasticity, thereby closing the inlets of the spaces 43. Accordingly, by turning on or off the current supply for generating heat in the thermal wire 47, the inlets of the spaces 43 are opened or closed. As a result, the release of the odor compound 45 may be controlled.

Figure 6:
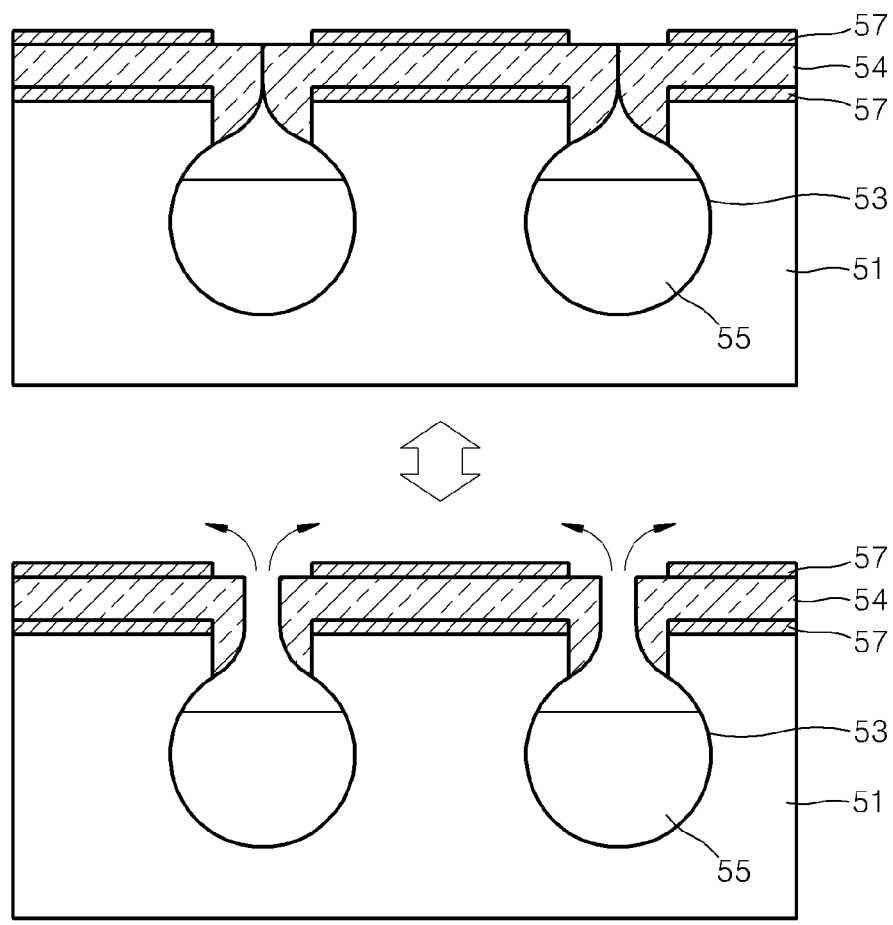
FIG. 6 is a schematic view of an odor compound release device according to another embodiment.

FIG. 6 is a schematic view of an odor compound release device according to another embodiment. A substrate 51 includes a plurality of spaces 53 therein, and the spaces 53 are to be filled with an odor compound. The spaces 53 may have a diameter of a few micrometers or a few millimeters. A capping layer 54 may cover a surface of the substrate 51, and portions of the capping layer 54 contact each other to close inlets of the spaces 53. In this regard, the contact portions of the capping layer 54 are not sealed, so that when power is applied thereto, the portions of the capping layer 54 are separated from each other, thereby opening the inlets of the spaces 53.

The substrate 51 may be formed of various materials such as plastic, metal, silicon, etc. The spaces 53 in the substrate 51 may be formed by, for example, a MEMS process. Alternatively, the substrate 51 may be an anodic aluminum oxide substrate, and the spaces 53 in the anodic aluminum oxide substrate may be formed by anodic oxidation. The spaces 53 may be aligned in a matrix.

The capping layer 54 may be formed of a material that has a deformable state when voltage is applied thereto. The material will now be referred to as a voltage deformable material. The capping layer 54 may be formed of, for example, a conductive polymer, a liquid crystalline elastomer, or a dielectric elastomer.

The conductive polymer may be, for example, a homopolymer or copolymer, such as PA, PT, P3AT, PPY, PITN, PEDOT, PPV, poly (2,5-dialkoxy-para-phenylene vinylene), PPP, PPS, PHT, or P3HT, or PANI.

The liquid crystalline elastomer may be, for example, a monopolymer formed by curing polysiloxane, poly dimethyl siloxane, tetramethylenecyclosiloxane, or hydro-oligo dimethylsiloxane by hydrosilylation, or a copolymer of the monomer and polyester.

The dielectric elastomer may be, for example, silicone or acryl rubber.

Electrodes 57 may be formed on upper and lower surfaces of the capping layer 54 to apply voltage to the capping layer 54. The electrodes 57 may be disposed in location that enables inlets of the spaces 53 to be opened when the capping layer 54 is deformed by the voltage application.

Before voltage is applied, the capping layer 54 is not deformed and thus the inlets of the spaces 53 are maintained in a closed state. However, when voltage is applied, the capping layer 54 contracts and thus, the inlets of the spaces 53 are opened and an odor compound 55 is released from the spaces 53. When the voltage supply is stopped, the capping layer 54 changes from a contraction state to an original state, thereby closing the inlets of the spaces 53. Accordingly, by turning on or off the voltage supply, the inlets of the spaces 53 are opened or closed. As a result, the release of the odor compound 55 is controllable.

Figure 7:
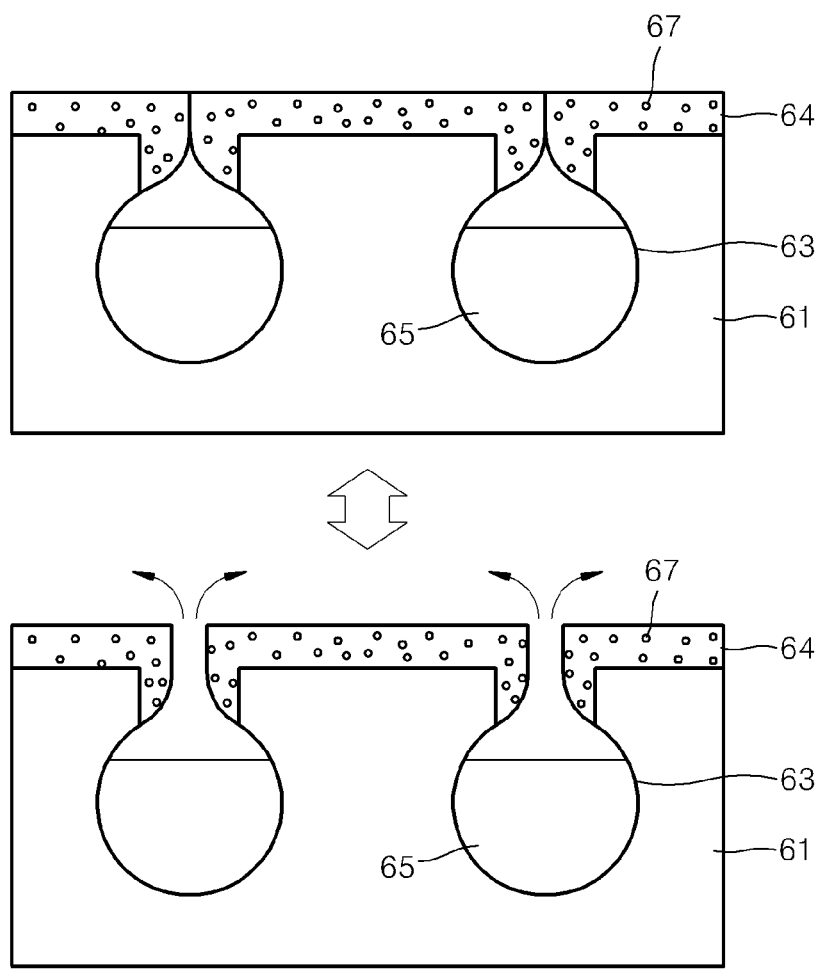
FIG. 7 is a schematic view of an odor compound release device according to another embodiment.

FIG. 7 is a schematic view of an odor compound release device according to another embodiment. A substrate 61 has a plurality of spaces 63 therein, and the spaces 63 are to be filled with an odor compound. The spaces 63 may have a diameter of a few micrometers or a few millimeters. A capping layer 64 may cover a surface of the substrate 61, and the inlets of the spaces 63 are closed by bring into contact portions of the capping layer 64. In this regard, the contact portions of the capping layer 64 are not sealed, so that when power is applied thereto, the contact portions of the capping layer 64 are separated from each other, thereby opening the inlets of the spaces 63.

The substrate 61 may be formed of various materials such as plastic, metal, silicon, etc. The spaces 63 in the substrate 61 may be formed by, for example, a MEMS process. Alternatively, the substrate 61 may be an anodic aluminum oxide substrate, and the spaces 63 in the anodic aluminum oxide substrate may be formed by anodic oxidation. The spaces 63 may be aligned in a matrix.

The capping layer 64 may be formed of a temperature-sensitive phase transition polymer including magnetic nanoparticles 67. The capping layer 64 changes from a hydrophilic state to a hydrophobic state according to its temperature. At a temperature lower than a phase transition temperature, the temperature-sensitive phase transition polymer absorbs water to expand, and at a temperature equal to higher than the phase transition temperature, the temperature-sensitive phase transition polymer has a hydrophobic state and releases water and contracts. The temperature-sensitive phase transition polymer may absorb water. The temperature-sensitive phase transition polymer may be, for example, PNIPAM. A phase transition temperature of PNIPAM is about 37° C.

At room temperature, the capping layer 64 has a hydrophilic state and expands, thereby closing the inlets of the spaces 63. If an external magnetic field is applied to the capping layer 64, the magnetic nanoparticles 67 in the support 61 are subjected to inductive heating and thus, the temperature of the capping layer 64 may increase to a temperature equal to or higher than a phase transition temperature. In this case, the capping layer 64 is deformed to a hydrophobic state and contracts, thereby opening the inlets of the spaces 63 and releasing an odor compound 65 to the outside. When the supply of the external magnetic field is stopped, the inductive heating of the magnetic nanoparticles 67 is stopped and the temperature of the capping layer 64 is decreased to a temperature lower than the phase transition temperature. At a temperature lower than the phase transition temperature, the capping layer 64 has a hydrophilic state and expands, thereby closing the inlets of the spaces 63.

Accordingly, by turning on or off the supply of an external magnetic field, the inlets of the spaces 63 are opened or closed. As a result, the release of the odor compound 65 is controllable.

Alternatively, instead of inclusion of the magnetic nanoparticles 67 in the capping layer 64, a thermal wire (not shown) may be introduced into the support 61 formed of the temperature-sensitive phase transition polymer to control the temperature of the support 61, thereby controlling the release of the odor compound 65.

In the above-described embodiments, spaces are conical or spherical. However, shapes of the spaces are not limited thereto, and other shapes may be used for the spaces, as would be understood by those skilled in the art. In addition, locations and shapes of a thermal wire and electrodes are not limited thereto, and may be appropriately changed as long as a support or a capping layer is deformed to open or close inlets of spaces.

Figure 8:
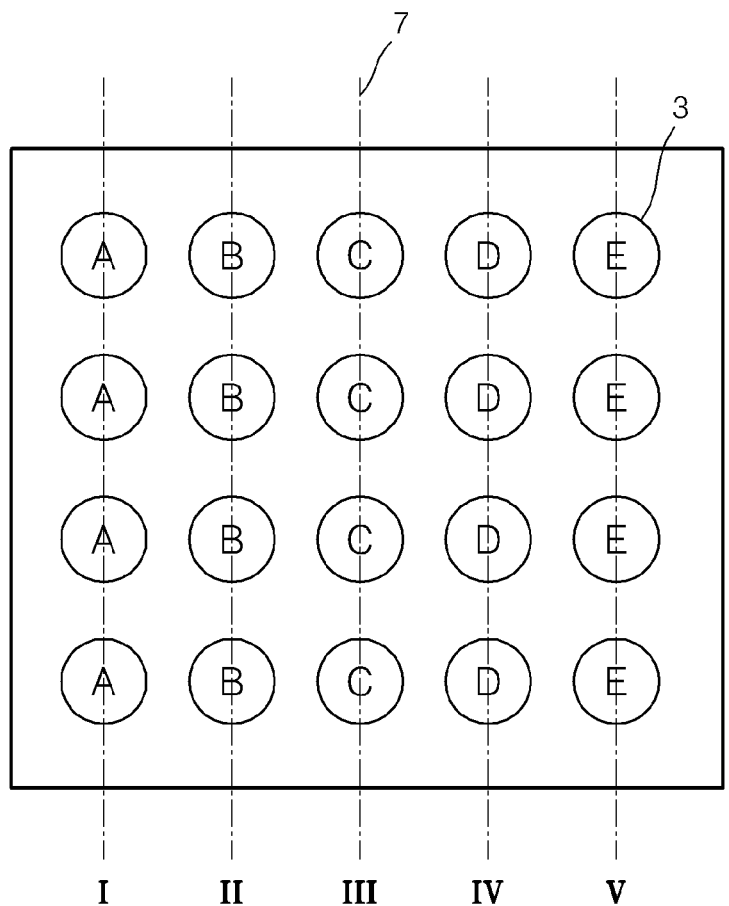
FIG. 8 is a schematic view of an odor compound release device according to another embodiment.

FIG. 8 is a plan view of schematically illustrating an alignment of spaces of an odor compound release device according to another embodiment. Spaces 3 are aligned in a matrix, and spaces 3 in columns I, II, III, IV, and V are respectively filled with odor compounds A, B, C, D, and E.

A thermal wire 7 may run under the spaces 3 in each column. In this case, an odor compound may be selectively released by supplying a current to the thermal wire 7 of a selected column. For example, odor compound A may be released by supplying a current to the thermal wire 7 in column I, and odor compound C may be released by supplying a current to the thermal wire 7 in column III.

Also, two or more odor compounds may be substantially simultaneously released by supplying a current to the thermal wires 7 in two or more columns. For example, odor compounds A and C may be simultaneously released by supplying a current to the thermal wires 7 in columns I and III. If the odor compounds A, B, C, D, and E filling the spaces 3 are fragrances, each of the fragrances may be selectively released, or two or more fragrances may be substantially simultaneously released to form a new fragrance.

Selectively, an alignment of electrodes may also be used to open or close the spaces 3 by selecting columns. For example, when a support or a capping layer is formed of a voltage deformable material, electrodes are formed in a line shape and aligned in columns. In this state, a column is selected and a voltage is applied to electrodes in the selected column, so that an odor compound may be selectively released.

Instead of columns, rows may be used to selectively release odor compounds. Alternatively, spaces may be grouped to selectively release odor compounds.

As described above, various odor compounds may be selectively released from one odor compound release device by aligning spaces filled with various odor compounds in a matrix, and selecting a row or column to open or close inlets of spaces corresponding to the selected row or column.

EXAMPLES

Figure 9:
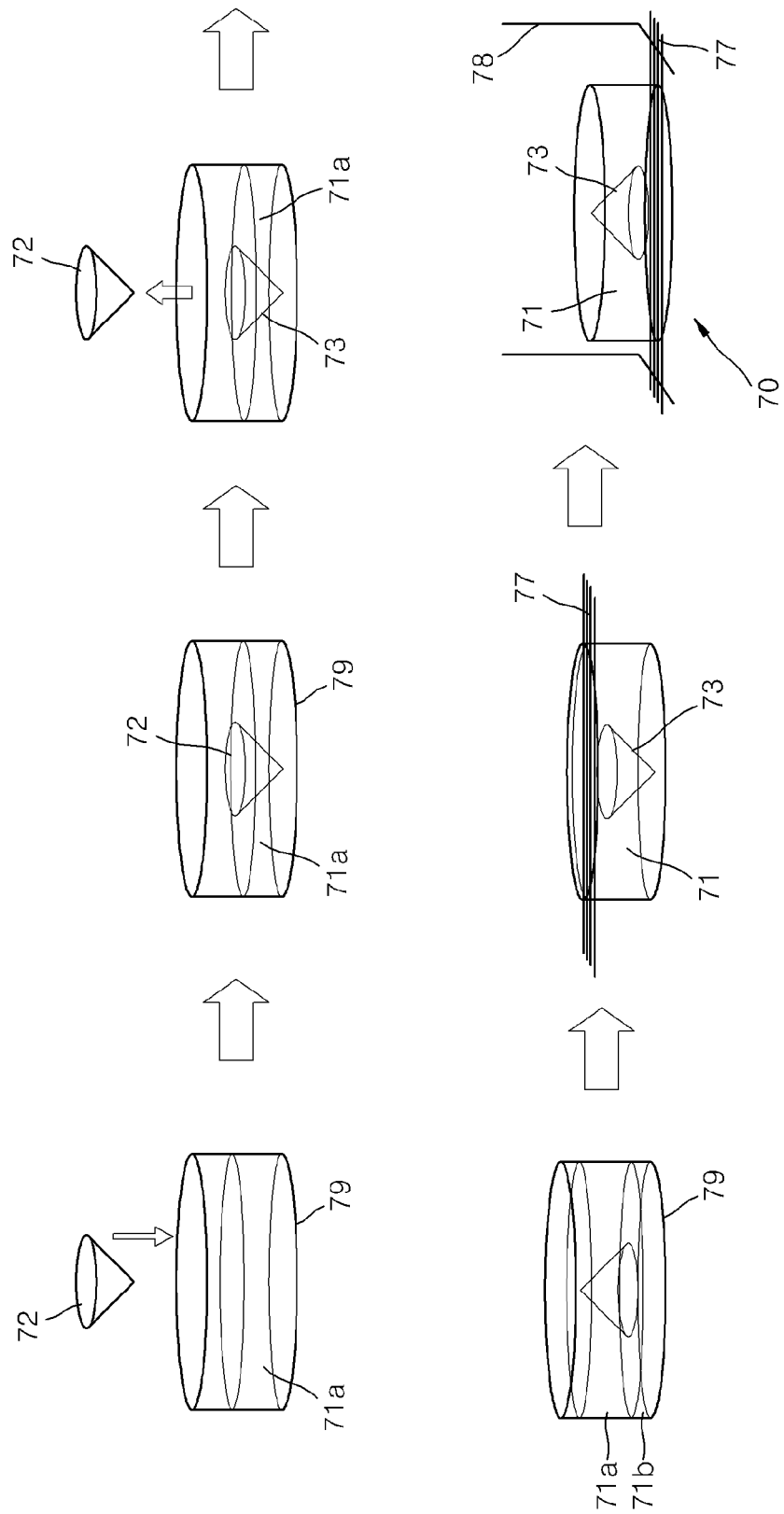
FIG. 9 shows views for schematically explaining a method of manufacturing an odor compound release device according to an embodiment.

FIG. 9 shows views for schematically illustrating a method of manufacturing an odor compound release device 70 according to an embodiment. A PDMS solution 71a is added to a container 79, and a template 72, which is conical, is placed in the container 79 in the PDMS solution 71a to form a space. In this regard, the template 72 is not completely immersed in the PDMS solution 71a so that a vertex and a bottom surface of the template 72 are exposed. The PDMS solution is prepared by mixing SYLGARD184, which was a product name, and a curing agent in a ratio of 10:1.

Then, the PDMS solution 71a is heat treated at a temperature of 80° C. for 30 minutes, and then, the template 72 is removed to form a space 73 in an upper portion 71a of a PDMS support, wherein the space 73 is conical. Separately, a PDMS solution 71b is added to the container 79 and then heat treated at a temperature of 80° C. for 30 minutes, thereby forming a lower portion 71b of the PDMS support.

The upper portion 71a of the PDMS support is attached to the lower portion 71b of the PDMS support to cover the bottom surface of the space 73, thereby completely forming a PDMS support 71. Since an inlet of the space 73 of the PDMS support 71 is the vertex of the cone, the inlet of the space 73 is closed.

Nichrome wires 77 are disposed on a lower surface of the PDMS support 71 and the nichrome wires 77 are connected to electrodes 78, thereby completely manufacturing the odor compound release device 70. Then, an ammonium hydroxide solution ($NH_3$, 14.8N) is injected to the space 73 of the PDMS support 71 by using a syringe.

Evaluation Example

Figure 10:
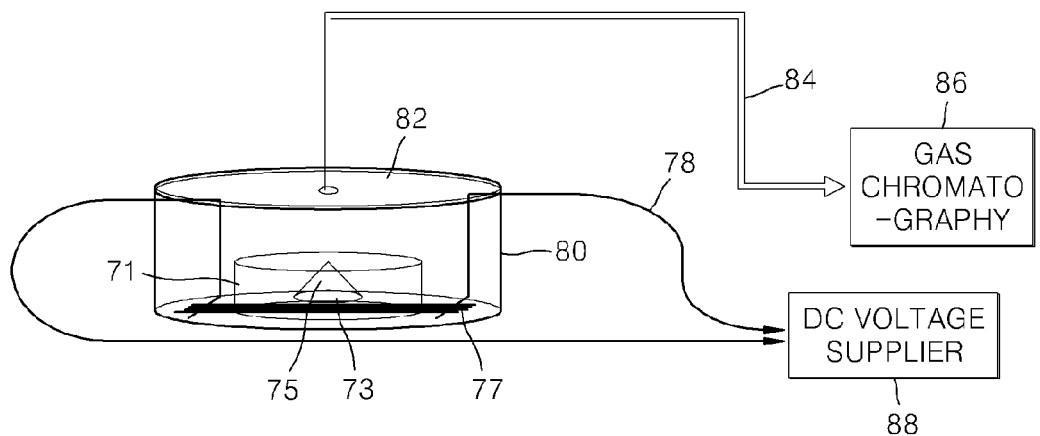
FIG. 10 is a view for explaining a method of evaluating driving of the odor compound release device described with reference to the embodiment of FIG. 9.

FIG. 10 is a view for explaining a method of evaluating driving of the odor compound release device 70 described with reference to the embodiment of FIG. 9. Referring to FIG. 10, the odor compound release device 70 including the support 71 in which the space 73 is filled with the ammonium hydroxide solution 75 is placed in a container 80, and the electrodes 78 are connected to a DC power supplier 88. Then, the container 80 is sealed with a cover 82 to which a tube 84 is connected to gas chromatography apparatus 86.

Figure 11:
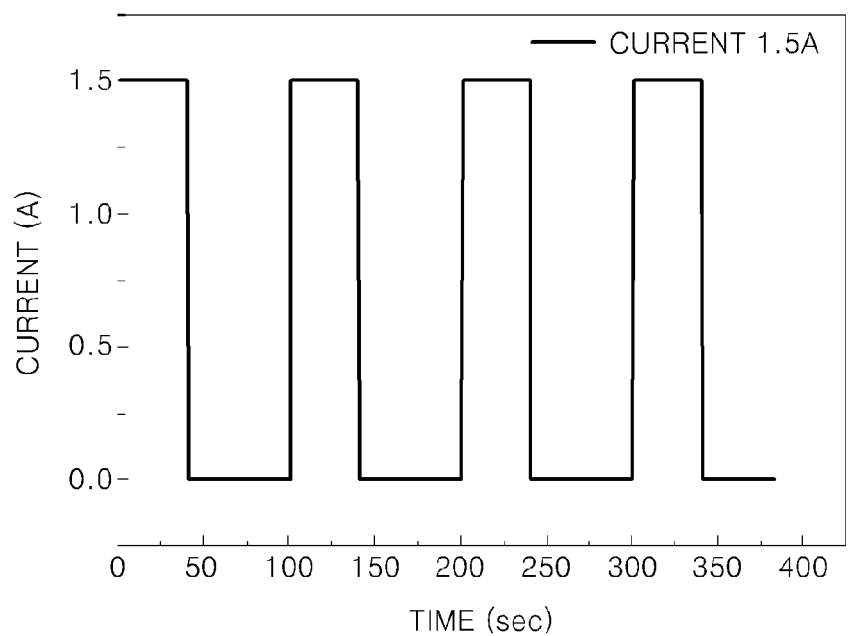
FIG. 11 shows a graph of a current pulse applied to an odor compound release device according to an embodiment.

FIG. 11 shows a graph of a current pulse applied to the odor compound release device 70 according to an embodiment. A current of about 1.5 A was supplied for about 40 seconds and then the current supply was stopped for about 60 seconds. The processes were repeatedly performed. When the current of about 1.5 A was supplied, the temperature of the nichrome wires 77 increased to about 100° C.

Figure 12:
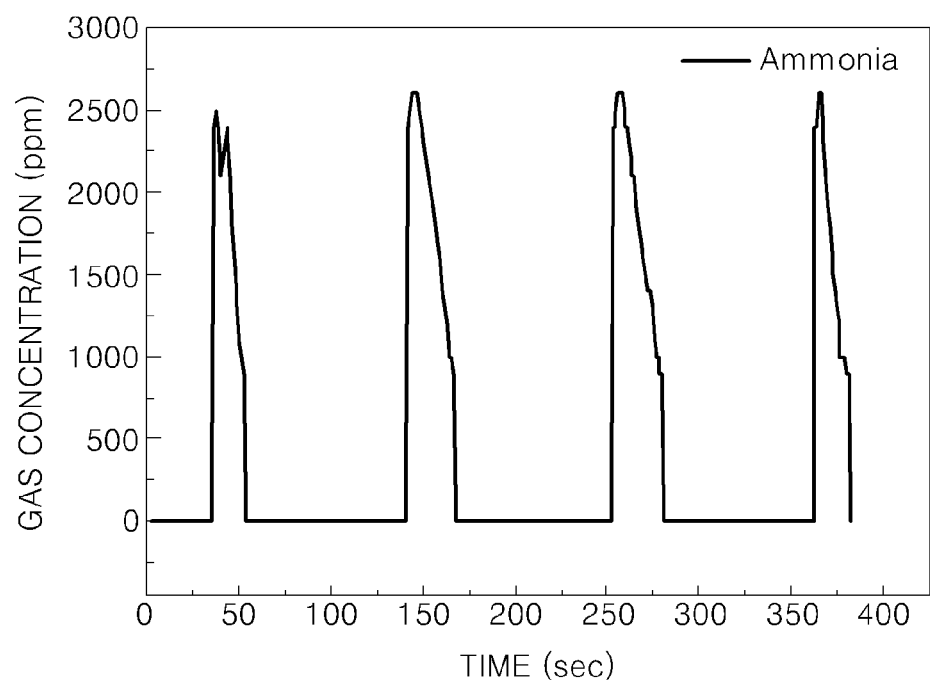
FIG. 12 shows a graph of an ammonia concentration with respect to time, detected by gas chromatography according to application of the current pulse of the embodiment of FIG. 11.

FIG. 12 shows a graph of ammonia concentration with respect to time, detected by gas chromatography according to application of the current pulse of the embodiment of FIG. 11. Referring to FIG. 12, corresponding to the current pulse type, ammonia is detected in a pulse type from the starting point of the current pulse. That is, when a current is turned on or off in a pulse pattern, ammonia is also turned on or off in a pulse pattern. The results show that release of an odor compound from the odor compound release device 70 is controlled by turning on or off the current supply.

As described above, according to the one or more of the above embodiments, in an odor compound release device, the release time and release amount of an odor compound are controlled by opening or closing an inlet of a space by using expansion or contraction of a support or capping layer due to an external stimulus such as heat or voltage.

It should be understood that the exemplary embodiments described herein should be considered in a descriptive sense only and not for purposes of limitation. Descriptions of features or aspects within each embodiment should typically be considered as available for other similar features or aspects in other embodiments.

What is claimed is:

1. An odor compound release device comprising:
   a support including a single layer of a plurality of internal spaces arranged in a plurality of arrays,
      wherein each of the plurality of internal spaces is configured to contain an odor compound and has an inlet at an outer surface of the support,
      wherein the inlet is opened by a deformation of the support in response to an application of a stimulus, and the inlet is closed by restoration of the support when the stimulus is not applied; and
   a member that is located in the support or on a surface of the support and is configured to apply the stimulus to the support,
   wherein inner surfaces of the support form the each of the plurality of internal spaces and the inner and outer surfaces of the support form the opening and the closure of the inlet.

2. The odor compound release device of claim 1, wherein the support comprises at least one of a natural rubber and a synthesized rubber.

3. The odor compound release device of claim 2, wherein the synthesized rubber comprises a material selected from the group consisting of a block copolymer, a fluorine rubber, a silicone rubber, and isoprene.

4. The odor compound release device of claim 2, wherein the member comprises a thermal wire configured to transfer heat to the support.

5. The odor compound release device of claim 4, wherein the thermal wire is disposed under the plurality of internal spaces.

6. The odor compound release device of claim 1, wherein the support comprises a material that is deformable when a voltage is applied thereto.

7. The odor compound release device of claim 6, wherein the support comprises at least one of a conductive polymer, a liquid crystalline elastomer, and a dielectric elastomer.

8. The odor compound release device of claim 6, wherein the member comprises an electrode configured to apply the voltage to the support.

9. The odor compound release device of claim 8, wherein the electrode is located on each of a first surface of the support and a second surface of the support which is opposite the second surface.

10. The odor compound release device of claim 1, wherein the support comprises a temperature sensitive phase transition polymer.

11. The odor compound release device of claim 10, wherein the support comprises poly(N-isopropylacrylamide) (PNIPAM).

12. The odor compound release device of claim 10, wherein the member comprises magnetic nanoparticles that are dispersed in the support and inductively heat the support when a magnetic field is applied.

13. The odor compound release device of claim 1, the member directly contacts the surface of the support.

14. An odor compound release device comprising:
- a substrate having a plurality of outer surfaces and including a single layer of a plurality of internal spaces arranged in a plurality of arrays, each of the plurality of internal spaces configured to contain an odor compound;
- a capping layer that is formed on an entire outer surface of the plurality of outer surfaces of the substrate and includes portions disposed at an inlet of the plurality of internal spaces that contact each other to close the inlet of the plurality of internal spaces, wherein the portions of the capping layer deform and separate to open the inlet of the plurality of internal spaces in response to an application of a stimulus, and are restored to contact each other when the stimulus is not applied; and
- a member that is located in the substrate or on a surface of the substrate and is configured to apply the stimulus to the capping layer,
- wherein inner surfaces of the substrate form the each of the plurality of internal spaces.

15. The odor compound release device of claim 14, wherein the capping layer comprises at least one of a natural rubber and a synthesized rubber.

16. The odor compound release device of claim 15, wherein the synthesized rubber comprises a material selected from the group consisting of a block copolymer, a fluorine rubber, a silicone rubber, and isoprene.

17. The odor compound release device of claim 16, wherein the member comprises a thermal wire configured to transfer heat to the capping layer.

18. The odor compound release device of claim 17, wherein the thermal wire is disposed under the plurality of internal spaces.

19. The odor compound release device of claim 14, wherein the capping layer comprises a material that is deformable when a voltage is applied thereto.

20. The odor compound release device of claim 19, wherein the capping layer comprises at least one of a conductive polymer, a liquid crystalline elastomer, or a dielectric elastomer.

21. The odor compound release device of claim 19, wherein the member comprises an electrode configured to apply the voltage to the capping layer.

22. The odor compound release device of claim 21, wherein the electrode is located on each of a first surface of the capping layer and a second surface of the capping layer that is opposite to the first surface.

23. The odor compound release device of claim 14, wherein the capping layer comprises a temperature-sensitive phase transition polymer.

24. The odor compound release device of claim 23, wherein the capping layer comprises poly(N-isopropylacrylamide) (PNIPAM).

25. The odor compound release device of claim 23, wherein the member comprises magnetic nanoparticles that are dispersed in the capping layer and inductively heat the capping layer when a magnetic field is applied.

26. The odor compound release device of claim 14, wherein the plurality of internal spaces is aligned in a matrix, and each of the spaces is distinguished from each other by a column and a row of the matrix.

27. The odor compound release device of claim 26, wherein the member is aligned such that the stimulus is independently applied to each row or each column of the matrix.

28. The odor compound release device of claim 14, the member directly contacts the surface of the substrate.

* * * * *